United States Patent
Serban et al.

(10) Patent No.: US 8,747,750 B2
(45) Date of Patent: Jun. 10, 2014

(54) FLUORESCENCE QUENCHING BASED OXYGEN SENSOR

(75) Inventors: Bogdan Catalin Serban, Bucharest (RO); Mihai N. Mihaila, Bucharest (RO); Octavian Buiu, Bucharest (RO)

(73) Assignee: Honeywell International Inc., Morristown, NJ (US)

( * ) Notice: Subject to any disclaimer, the term of this patent is extended or adjusted under 35 U.S.C. 154(b) by 149 days.

(21) Appl. No.: 13/308,992

(22) Filed: Dec. 1, 2011

(65) Prior Publication Data

US 2012/0164031 A1 Jun. 28, 2012

(30) Foreign Application Priority Data

Dec. 3, 2010 (EP) ..................... 10193624

(51) Int. Cl.
G01N 21/64 (2006.01)
G01N 21/76 (2006.01)
G01N 1/22 (2006.01)
G01N 7/00 (2006.01)

(52) U.S. Cl.
USPC .......... 422/82.08; 422/83; 436/164; 436/172; 436/68; 73/23.2; 73/23.3

(58) Field of Classification Search
USPC ..................... 422/82.08; 524/577; 525/333.3; 428/441
See application file for complete search history.

(56) References Cited

U.S. PATENT DOCUMENTS

2003/0235513 A1   12/2003   Keisuke et al.

FOREIGN PATENT DOCUMENTS

GB   1190583   5/1970

OTHER PUBLICATIONS

"European Application Serial No. 10193624.3, Response filed Sep. 27, 2011 to Office Action mailed Apr. 4, 2011", 3 pgs.
"European Application Serial No. 10193624.3, European Search Report mailed Apr. 4, 2011", 9 pgs.
Amao, Y., et al., "Fluorescence quenching oxygen sensor using an aluminum phthalocyanine-polystyrene film", Analytica Chimica Acta, 407(1-2), (Feb. 29, 2000), 41-44.
Fujiwara, Y, et al., "An oxygen sensor based on the fluorescence quenching of pyrene chemisorbed layer onto alumina plates", Sensors and Actuators. 89(1-2), (Mar. 1, 2003), 187-191.
Serban, B., et al., "Calixarene-Doped Polyaniline for Applications in Sensing", IEEE International Semiconductor Conference, 2006, (2006), 257-260.
Teertstra, S J, et al., "Comparison of the long range polymer chain dynamics of polystyrene and cis-polyisoprene using polymers randomly labeled with pyrene", vol. 50, No. 23, (Nov. 3, 2009), 5456-5466.
Winnik, M A, et al., "Cyclization dynamics of polymers: 10 Synthesis, fractionation,and fluorescent spectroscopy of pyrene end-capped polystyrenes", vol. 25, No. 1 (Jan. 1, 1984), 91-99.
Wolfbeis, Otto S., "Materials for fluorescence-based optical chemical sensors", J. Mater. Chem., 15, (2005), 2657-2669.
Xu, W., et al., "Oxygen Sensors Based on Luminescence Quenching: Interactions of pyrene with the Polymer Supports", Analytical Chemistry, 67(18), (1995), 3172-3180.

*Primary Examiner* — Neil N Turk
(74) *Attorney, Agent, or Firm* — Schwegman, Lundberg and Woessner, P.A.

(57) ABSTRACT

A fluorescence quenching based oxygen sensor can be prepared comprising a polystyrene polymer linked to pyrene. The fluorescence based sensor has the formula (I), Polystyrene—Y—R—Pyrene   (I);

wherein Y is fluorescence quenching

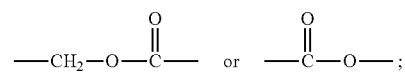

and
R is an aliphatic linking group having 1 to 11 carbon atoms. The sensor can be coated onto a support and integrated with an LED excitation source and fluorescence detector.

15 Claims, No Drawings

FLUORESCENCE QUENCHING BASED OXYGEN SENSOR

PRIORITY CLAIM AND RELATED APPLICATION

This application claims the benefit of priority under 35 U.S.C. Section 119 to European Patent Application Ser. No. 10193624.3, filed Dec. 3, 2010, which application is incorporated herein by reference in its entirety.

FIELD OF THE INVENTION

This invention relates to fluorescence based oxygen sensors using pyrene bound to a polymer and to methods of preparing these sensors.

BACKGROUND

Determination of oxygen concentration is important in various fields such as automotive applications, medical devices, anesthesia monitors, and environmental monitoring. Recently, devices based on the fluorescence quenching of organic molecules have been developed to determine the concentration of oxygen. When exposed to light at an appropriate wavelength, the fluorescent substances absorb energy and are promoted from their ground state energy level (So) into an excited state energy level (S1). Fluorescent molecules are unstable in their excited states and can relax by different competing pathways.

Fluorescence based oxygen sensing elements work on the principle that relaxation of the S1 state can also occur through interaction with a second molecule through fluorescence quenching. Molecular oxygen ($O_2$) is an efficient quencher of fluorescence because of its unusual triplet ground state. Fluorophores used for oxygen sensing include: pyrene and its derivatives, quinoline, decacyclene and its derivatives, phenanthrene, erythrosine B, and aluminum 2,9,16,23-tetraphenoxy-29H,31H-phthalocyaninehydroxide. These fluorophores are incorporated into a polymer matrix such as: silicones, polystyrene, and ethyl cellulose that are selectively permeable to oxygen and adhere to glass.

One difficulty with incorporating fluorescent molecules into a polymer is that the fluorescent molecule may have poor solubility and may crystallize or aggregate within the polymer matrix upon coating and drying.

It would be useful to provide an oxygen sensor that does not crystallize or aggregate within the polymer matrix upon coating and drying.

SUMMARY

A fluorescence quenching oxygen sensor comprises a support having coated thereon, one or more of a polystyrene polymer linked to pyrene represented by Polystyrene-Y—R-Pyrene (I); wherein Y is

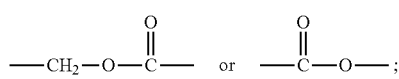

and
R is an aliphatic linking group having 1 to 11 carbon atoms.

A composition comprises a polystyrene polymer linked to a pyrene represented by formula (I), Polystyrene-Y—R-Pyrene (I); wherein Y is

and
R is an aliphatic linking group having 1 to 11 carbon atoms.

A method of preparing a fluorescence quenching oxygen sensor comprises coating onto a support a solution of one or more of a polystyrene polymer linked to pyrene represented by formula (I), Polystyrene-Y—R-Pyrene (I); wherein Y is

and
R is an aliphatic linking group having 1 to 11 carbon atoms.

Other aspects, advantages, and benefits of the present invention are apparent from the detailed description, examples, and claims provided in this application.

DETAILED DESCRIPTION

We have found that attachment of a pyrene fluorophore to a styrene polymer through a covalent bond prevents aggregation and crystallization of the pyrene from the polystyrene polymer matrix and provides a material that can be used as a fluorescence quenching oxygen sensor.

In one embodiment the fluorescence quenching oxygen sensor comprises a polystyrene polymer linked to a pyrene represented by Polystyrene-Y—R-Pyrene (I); wherein Y is

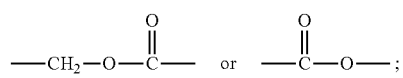

and R is an aliphatic linking group having 1 to 11 carbon atoms.

In one embodiment the pyrene is 1-pyrene. In one embodiment, attachment is by an ester linkage having the structure

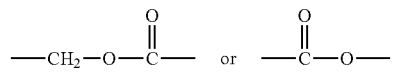

The ester linkage may formed by reaction of a para-substituted polystyrene polymer carboxylic acid with a pyrene alkanol, or by the reaction of a para-substituted polystyrene polymer alcohol with a pyrene alkanecarboxylic acid (or carboxylate salt).

Polystyrene is a useful polymer as it is inexpensive, selectively permeable to oxygen, and adheres to various substrates. In one embodiment, the polymer of the oxygen sensor is a para-substituted polystyrene having the formula:

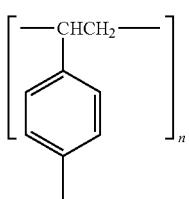

wherein n represents the degree of polystyrene polymerization and attachment of the Y group is at the para position.

Representative pyrene based fluorophores include: pyrene butyric acid, pyrene decanoic acid, pyrene dodecanoic acid, pyrene methanol, pyrene butanol, and pyrene acetic acid.

Specific pyrene based fluorophores include: 1-pyrene butyric acid (1), 1-pyrene decanoic acid (2), 1-pyrene dodecanoic acid (3), 1-pyrene methanol (4), 1-pyrene butanol (5), and 1-pyrene acetic acid (6). These pyrene carboxylic acids and pyrene alcohols are commercially available from Sigma-Aldrich (St. Louis, Mo.).

Structure (1) represents 1-pyrenebutyric acid.

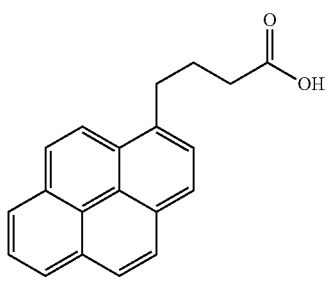
(1)

Structure (2) represents 1-pyrenedecanoic acid.

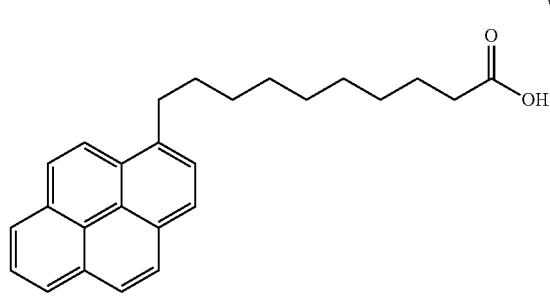
(2)

Structure (3) represents 1-pyrenedodecanoic acid.

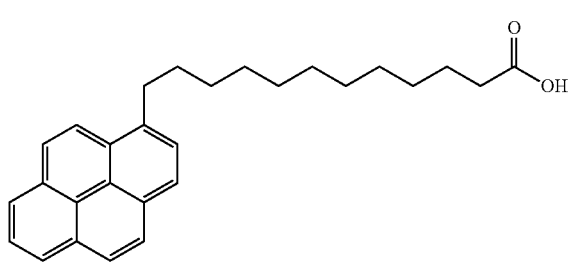
(3)

Structure (4) represents 1-pyrene methanol.

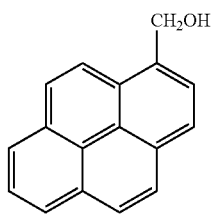
(4)

Structure (5) represents 1-pyrene butanol.

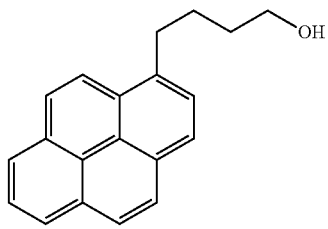
(5)

Structure (6) represents 1-pyrene acetic acid.

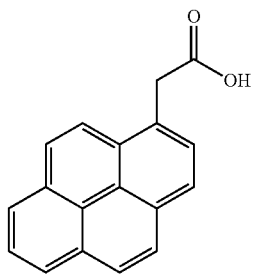
(6)

Representative polymers represented by Polystyrene-Y—R-Pyrene include:

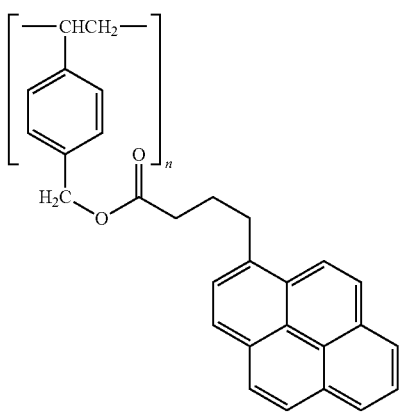
(7)

(8)
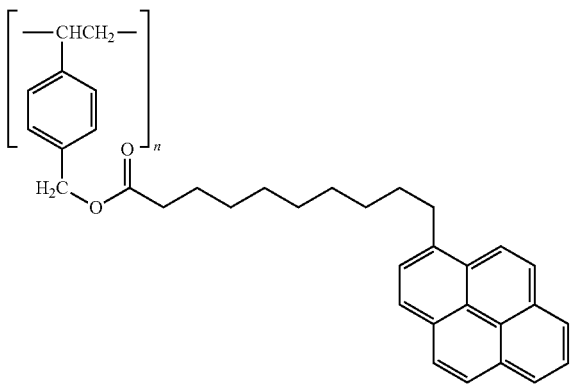

(9)
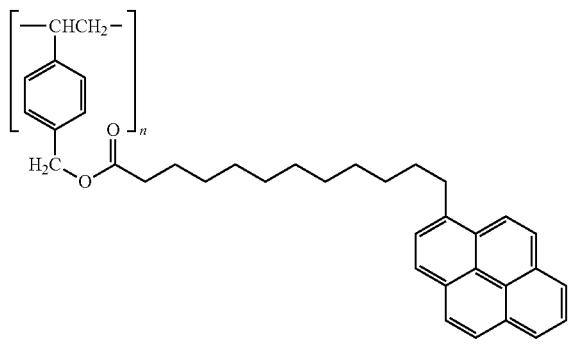

(10)
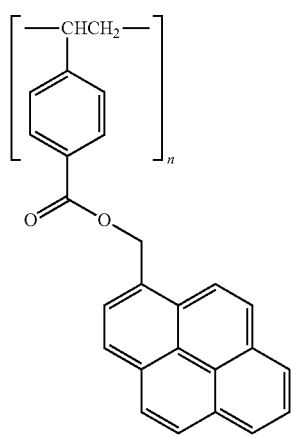

(11)
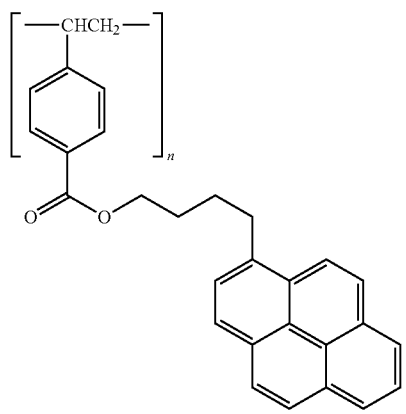

(12)
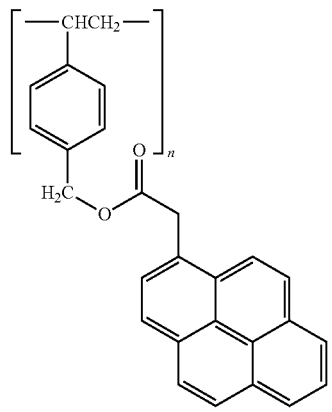

In formula (I) R is an aliphatic linking group having from 1 to 11 carbon atoms. The aliphatic linking group may be straight chain or branched and may contain various substituents such as aliphatic groups (e.g., methyl, ethyl, propyl, iso-propyl, sec-butyl, etc.). In one embodiment, R is a straight chain alkylene group —$(CH_2)_m$— having from 1 to 11 methylene groups.

In one embodiment the oxygen sensor comprises a support. The support may be transparent, translucent, or opaque. The support may be rigid or flexible. Exemplary polymeric materials for making such supports include polyesters [such as poly(ethylene terephthalate) and poly(ethylene naphthalate)], cellulose acetate and other cellulose esters, polyvinyl acetal, polyolefins, polycarbonates, and polystyrenes. Preferred polymeric supports include polymers having good heat stability, such as polyesters and polycarbonates. Support materials may also be treated or annealed to reduce shrinkage and promote dimensional stability. Opaque supports can also be used, such metals and resin-coated papers that are stable to high temperatures. Rigid supports such as glass are also useful.

The fluorescence quenching oxygen sensor can be prepared by coating one or more of the Polystyrene-Y—R-Pyrene compounds of formula (I) onto a support using various coating procedures including spin coating, wire wound rod coating, dip coating, air knife coating, curtain coating, slide coating, or extrusion coating.

Preparation of Compounds of Formula (II)

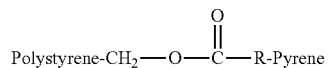

The preparation of compounds of formula (II) is shown below in Reaction Scheme (I)

Polystyrene is chloromethylated using chloromethyl methyl ether in the presence of zinc chloride (step 1). The chloromethylated polystyrene is treated with sodium iodide in acetone (Finkelstein reaction) to form iodomethyl polystyrene (step 2). Iodomethyl polystyrene is condensed with the carboxylic acid salt of a 1-pyrene alkylene carboxylic acid at elevated temperature in the presence of tetramethylammonium iodide as a phase transfer catalyst to form a compound of formula (II) (step 3).

Preparation of Compounds of Formula (III)

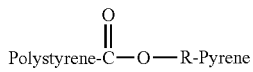
(III)

The preparation of compounds of formula (III) is shown below in Reaction Scheme (II)

Friedel-Crafts acylation of polystyrene in the presence of aluminum chloride in is carried out in a solvent such as nitrobenzene or carbon disulfide to provide acylated polystyrene (step 1). The acyl group is oxidized with sodium hypochlorite and acidified to form polystyrene carboxylic acid (step 2). The carboxylic acid is then reacted with a pyrene alkanol in the presence of dicyclohexyl dicarboximide (DCC) in dimethyl sulfoxide (DMSO) to form a compound of formula (III).

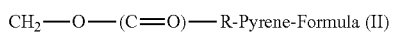
Scheme (I)-Preparation of Polystyrene-
CH₂—O—(C═O)—R-Pyrene-Formula (II)

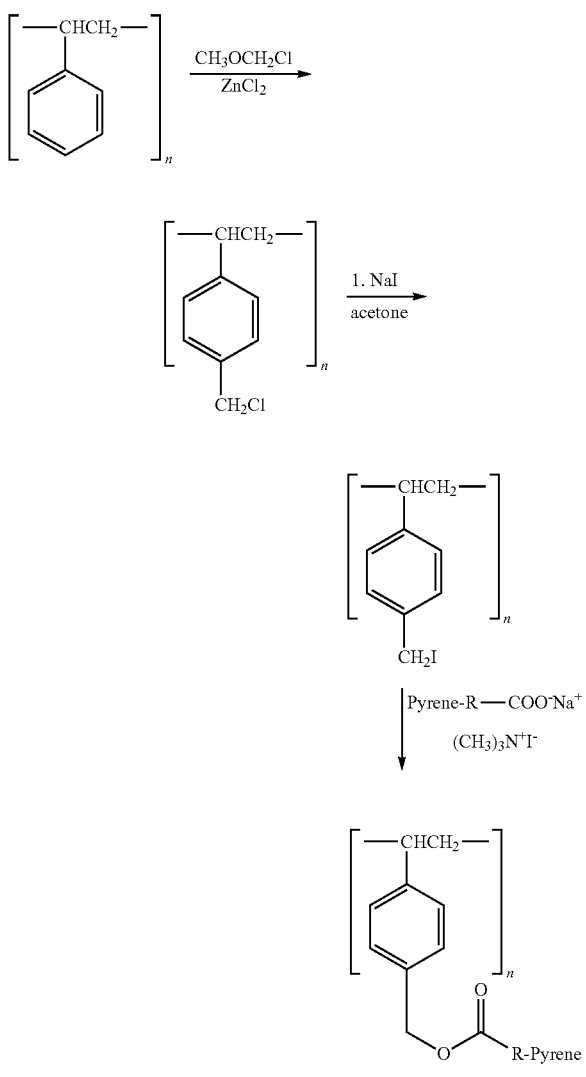

Scheme (II)-Preparation of Polystyrene-(C═O)—O—R-Pyrene-Formula (III)

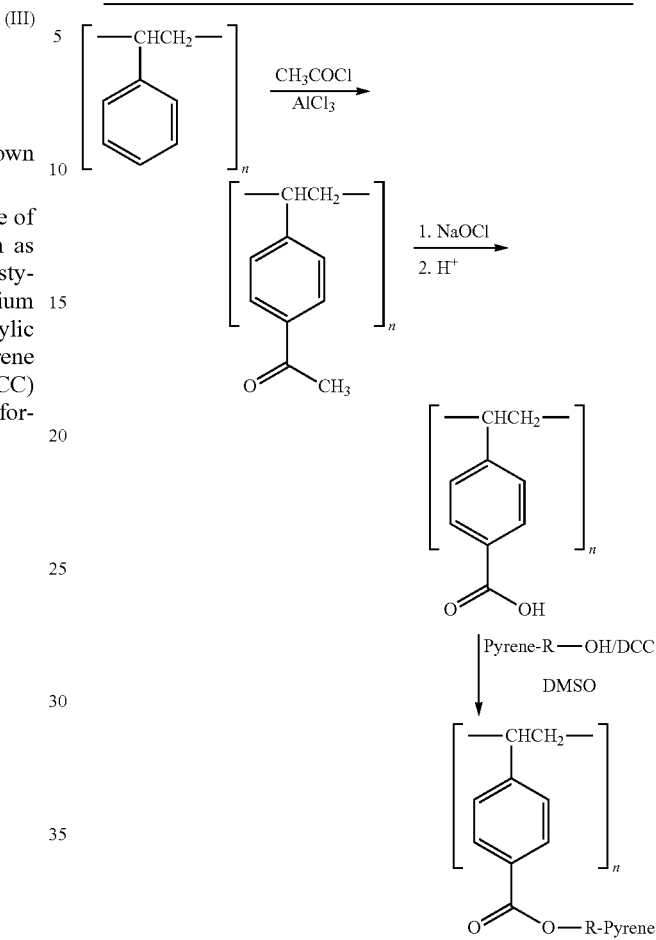

Preparation of Fluorescence Quenching Oxygen Sensors

One or more fluorescent polystyrene polymers represented by formula (I) is dissolved in an appropriate solvent to form a homogeneous solution. The solution is coated onto a glass slide to form a film. The coated slide is stored for three days, after which the film is dried in vacuo at 50° C. for three hours. The film is then dried in a dessicator for three weeks.

Use of the Oxygen Sensor

The oxygen sensor may be incorporated in a miniature solid-state transducer that uses fluorescence to measure oxygen partial pressure. An LED excitation source and fluorescence detector are both integrated into the device. The device has a strong response to oxygen ($O_2$) but is insensitive to common atmospheric and medical gases. The Polystyrene-Y—R-Pyrene (or mixtures thereof) is excited by the LED with an appropriate wavelength and fluoresces. Upon exposure to oxygen the fluorescence rapidly decays. The intensity and rate of decay of the fluorescence is measured by the detector.

REFERENCES

Otto S. Wolfbeis, "Materials for fluorescence-based optical chemical Sensors," *J. Mater., Chem.*, 15, 2657-2669 (2005).

Wenying et al., "Oxygen sensors based on luminescence quenching: interactions of pyrene with the polymer supports," *Analytical Chem.*, 67, 3172-3180 (1995).

The invention claimed is:

1. A fluorescence quenching oxygen sensor comprising:
a support having coated thereon,
one or more of a polystyrene polymer linked to a pyrene represented by formula (I), Polystyrene-Y—R-Pyrene (I);

wherein Y is

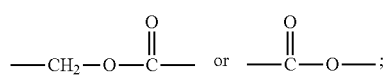

and
R is an aliphatic linking group having 1 to 11 carbon atoms.

2. The fluorescence quenching oxygen sensor of claim 1, wherein the polystyrene is a para-substituted polystyrene having the formula:

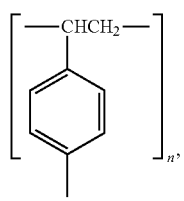

wherein n represents the degree of polystyrene polymerization.

3. The fluorescence quenching oxygen sensor of claims 1 or 2, wherein R is —$(CH_2)_m$—, and m is 1 to 11.

4. The fluorescence quenching oxygen sensor of claim 1, wherein the pyrene is 1-pyrene.

5. The fluorescence quenching oxygen sensor of claim 1, wherein —Y—R-Pyrene Pyrene is represented by one or more of:

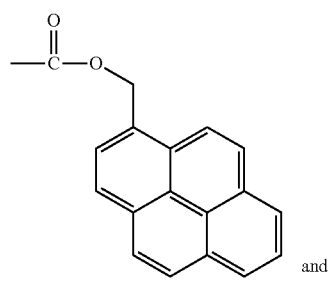

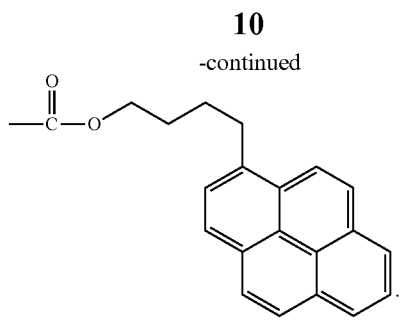

6. The fluorescence quenching oxygen sensor of claim 1, wherein —Y—R-Pyrene is represented by one or more of:

7. The fluorescence quenching oxygen sensor of claim 1, wherein the support is glass.

8. The fluorescence quenching oxygen sensor of claim 1, further comprising an LED excitation source and a fluorescence detector.

9. The fluorescence quenching oxygen sensor of claim 1, wherein the Polystyrene-Y—R-Pyrene (I) is represented by one or more of:

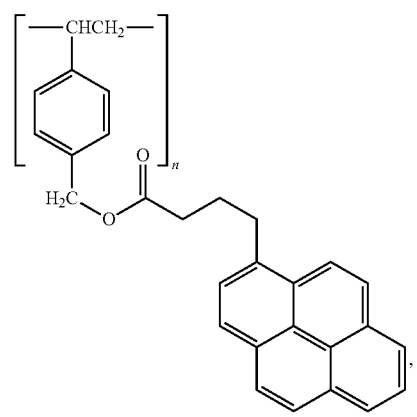
(7)

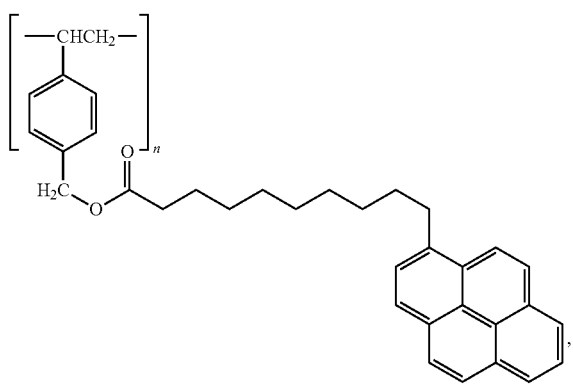
(8)

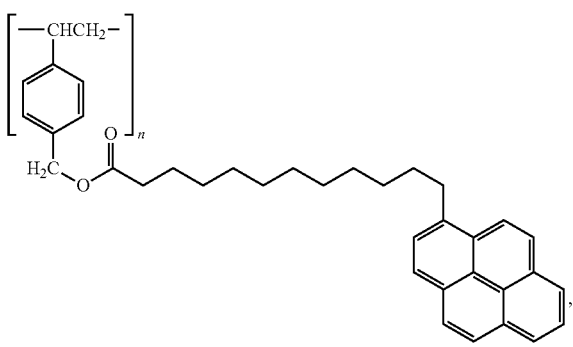
(9)

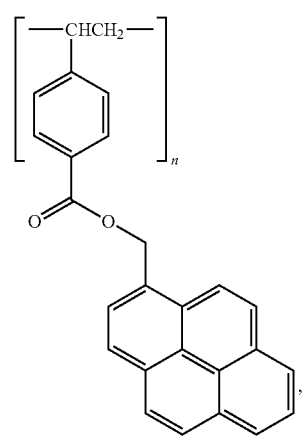
(10)

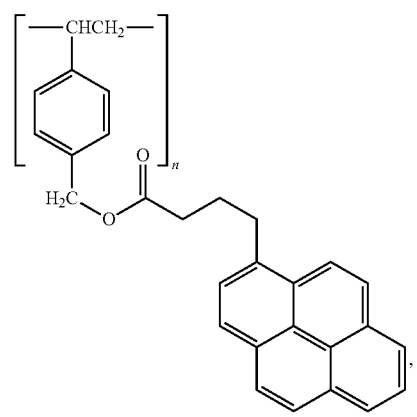
(11), and

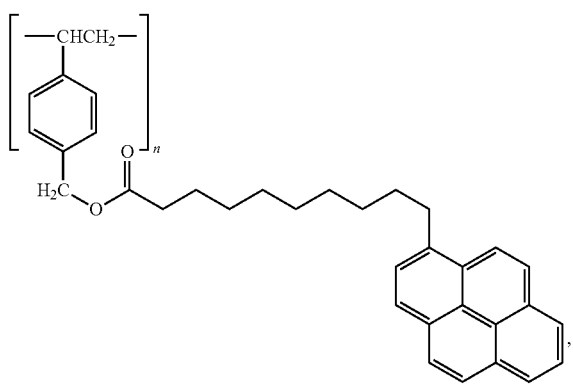
(12); and wherein n represents the degree of polystyrene polymerization.

10. A composition comprising:
   a polystyrene polymer linked to a pyrene represented by formula (I), Polystyrene-Y—R-Pyrene (I);

wherein Y is

and
   R is an aliphatic linking group having 1 to 11 carbon atoms.

11. The composition of claim 10 wherein the polystyrene is a para-substituted polystyrene having the formula:

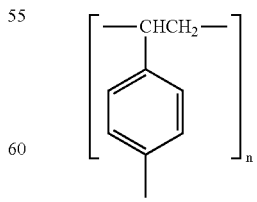

wherein n represents the degree of polystyrene polymerization.

12. The composition of claim 10 or 11, wherein R is —(CH$_2$)$_m$—, and m is 1 to 11.

13. The fluorescence quenching oxygen sensor of claim 1, wherein the Polystyrene-Y—R-Pyrene (I) is represented by one or more of:

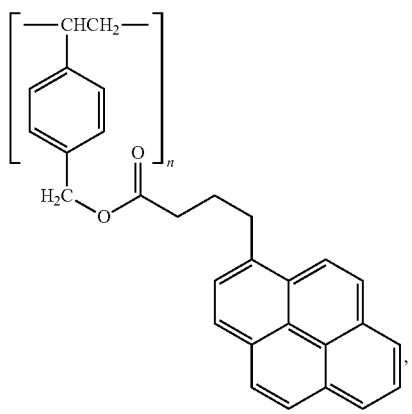
(7)

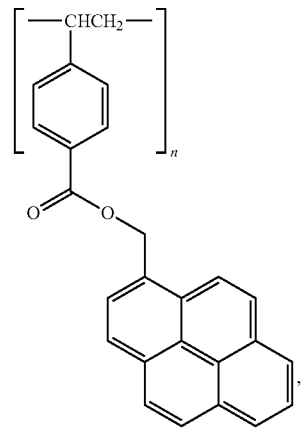
(10)

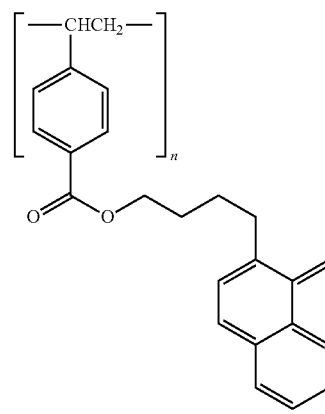
(11)

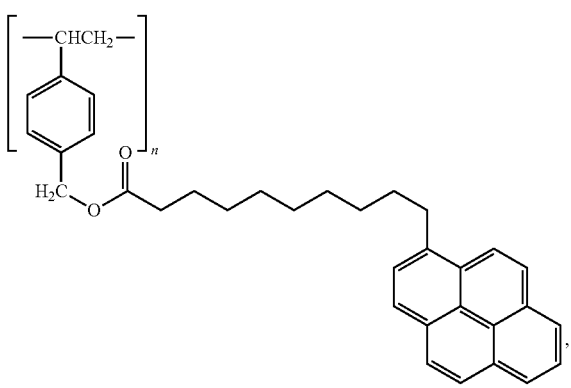
(8)

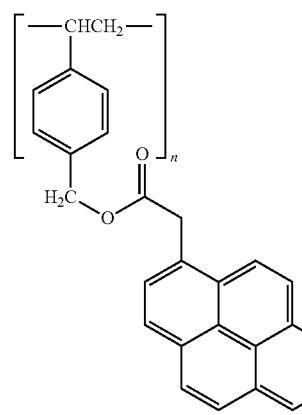
(12)

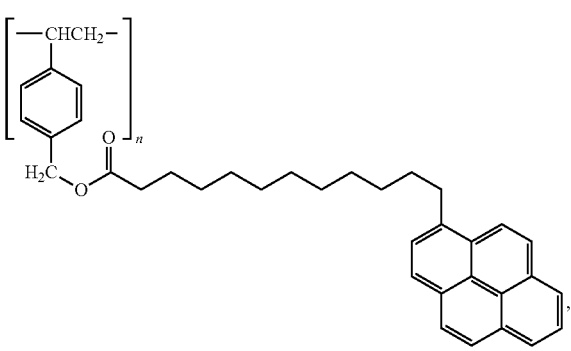
(9)

wherein n represents the degree of polystyrene polymerization.

14. A method of preparing an oxygen sensor of claim 1, comprising coating onto a support a solution of:
one or more of a polystyrene polymer linked to pyrene represented by formula (I), Polystyrene-Y—R-Pyrene  (I);

wherein Y is

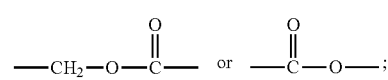

and
R is an aliphatic linking group having 1 to 11 carbon atoms.
15. The method of claim 14, wherein Polystyrene-Y—R-Pyrene (I) is represented by one or more of:
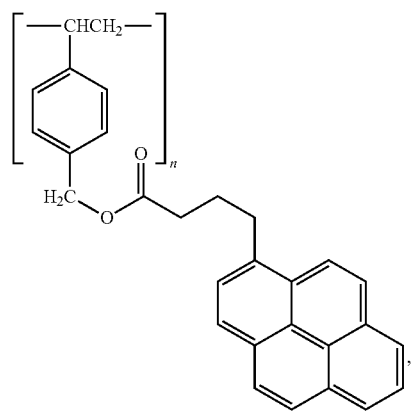
(7)
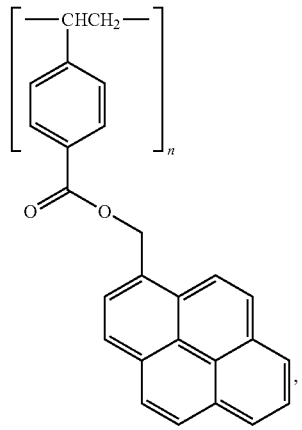
(10)
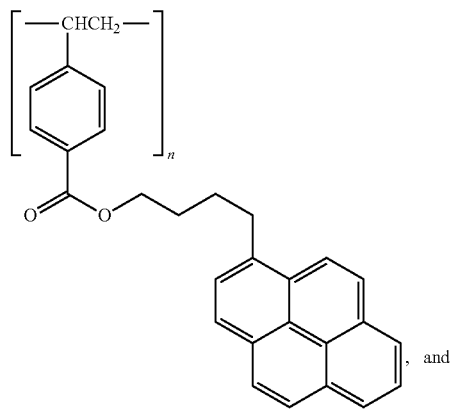
(8)
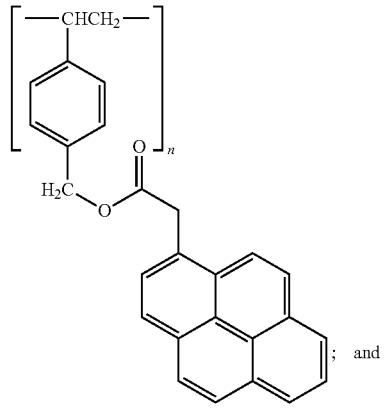
(11)
(9)
(12)
wherein n represents the degree of polystyrene polymerization.
* * * * *